(12) United States Patent
Mackool (10) Patent No.: US 9,011,470 B2
(45) Date of Patent: Apr. 21, 2015

(54) TORIC AXIS MARKER

(71) Applicant: Richard Jonathan Mackool, Astoria, NY (US)

(72) Inventor: Richard Jonathan Mackool, Astoria, NY (US)

( * ) Notice: Subject to any disclaimer, the term of this patent is extended or adjusted under 35 U.S.C. 154(b) by 105 days.

(21) Appl. No.: 13/836,960

(22) Filed: Mar. 15, 2013

(65) Prior Publication Data

US 2014/0277016 A1  Sep. 18, 2014

(51) Int. Cl.
*A61F 9/00* (2006.01)
*A61F 9/013* (2006.01)

(52) U.S. Cl.
CPC .................... *A61F 9/0136* (2013.01)

(58) Field of Classification Search
CPC ..... A61F 9/0133; A61F 9/013; A61F 9/0136; A61F 9/007; A61F 9/00754; A61F 9/00736; A61F 9/00836; A61F 2009/00872; A61F 2/142; A61F 2/14
USPC ......... 606/166, 167, 170, 172, 107, 161, 4–6, 606/1; 604/22, 521; 623/6.11, 6.12, 4.11; 351/212; 73/387; 116/284, 285
See application file for complete search history.

(56) References Cited

U.S. PATENT DOCUMENTS

| | | | |
|---|---|---|---|
| 4,406,285 A | 9/1983 | Villasenor | |
| 4,417,579 A | 11/1983 | Soloviev | |
| 4,440,168 A | 4/1984 | Warren | |
| 4,515,157 A | 5/1985 | Fedorov | |
| 4,739,761 A * | 4/1988 | Grandon | 606/166 |
| 5,184,405 A | 2/1993 | Cress | |
| 5,314,439 A | 5/1994 | Sugita | |
| 6,217,596 B1 | 4/2001 | Farah | |
| 2009/0254108 A1* | 10/2009 | Davis | 606/166 |

* cited by examiner

*Primary Examiner* — Jocelin Tanner
(74) *Attorney, Agent, or Firm* — Charles C. McCloskey (57) ABSTRACT

A toric axis marker has a handle, a coaxial tip, a head upon the tip, a dial axially above the head, and a marker head with two blades connecting to the dial. The dial and blades rotate simultaneously and concentrically upon the head. The head and its components have a central aperture for a surgeon to use in positioning the marker relative to the center of an eye. The marker head has its two blades upon a common diameter. The dial has two symmetric arcuate windows that reveal an angle scale. The marker body has an inwardly offset angle to the handle. Each blade has a blunt edge outwardly from the marker head and a slightly curved shape that conforms to the shape of an eyeball, proximate the cornea. With the blades positioned, a surgeon marks the cornea with an ink for incision locations.

13 Claims, 3 Drawing Sheets

TORIC AXIS MARKER

BACKGROUND OF THE INVENTION

The toric axis marker generally relates to ophthalmology and more specifically to marking the cornea at one or more meridians. The invention relates to placing markings precisely upon a cornea before a surgeon incises the cornea during procedures such as astigmatic keratotomy, limbral relaxing incisions, radial keratotomy, other corneal incisions, other corneal procedures, or a lens replacement.

Developed over the millennia, people have eyes to see. An eye has various tissues that receive and focus light upon a retina that converts the light into electrical signals transmitted to a person's brain for interpretation. In the vicinity of a person, light encounters a cornea as the first part of the eye. The cornea, generally transparent, admits light further into the eye. The cornea has its own constituent parts where the endothelium is the extremely thin, innermost layer of the cornea. Inwardly from the cornea, an eye has its lens of flexible tissue.

Various fine muscles attach to the lens and stretch the lens to adjust its focus as desired by the person seeing an object at a certain distance. The soft lens seeks to modify the focal power of the lens within an eye. The eye lens, inwardly from the cornea, provides the focusing for images. The eye lens comes from concentric protein layers that move well during the youth of a person but then gradually thicken and lose pliability over the years. Reaching the age of forty years, many people then encounter difficulty in focusing because of this eye lens thickening, or presbyopia. Then later in a person's life, the lens may become opaque, creating a condition known as a cataract.

To correct myopia and to some extent presbyopia, surgeons developed the technique of radial keratotomy, also known as RK. The RK technique involves incising the cornea with a radial pattern of incisions. The incisions penetrate the corneal stroma to a predetermined depth. A surgeon uses a diamond bladed knife to make the narrow, deep incisions. The incisions alter the curvature of the cornea and improve the patient's vision.

In other situations, a surgeon makes incisions in the cornea to create a more spherical shape. This treatment of a condition called astigmatism may employ incisions that are tangential or circular to the center of the cornea.

Over a lifetime, the lens hardens, the lens muscles weaken, glaucoma strikes, a cataract grows, and a host of other maladies may affect the lens. Early on, a person's lens would just lose function and focal power. A person would compensate for that with glasses or prescription eye drops as needed. In time, a clouding of the lens can result in blindness. Recently decades have brought advances in both materials and surgical techniques. Surgeons may now replace a lens in a living eye.

In recent years, various physicians and lens manufacturers have attempted to duplicate the ability of a human eye lens to focus at both near and far distances and to remove an existing lens and to install a new lens without blinding a patient.

With RK, astigmatism incisions, and lens replacement, a surgeon incises the eye. The small thickness of the cornea, delicate nature of the eye, and importance of vision to a patient, the surgeon must make precise incisions accurately located. The surgeons utilize various tools often with assisted magnification to make such incisions.

DESCRIPTION OF THE PRIOR ART

Figure 3:
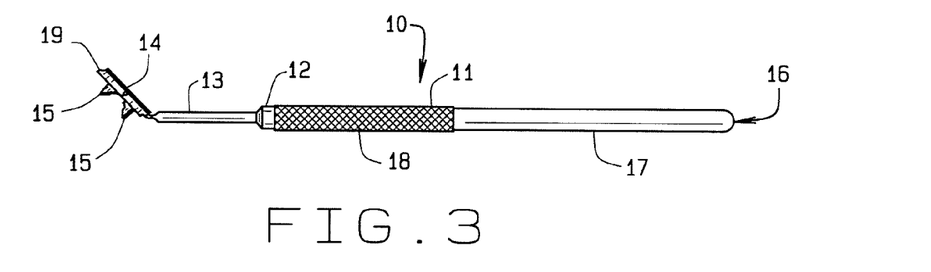
FIG. 3 provides a side view of the invention, approximately perpendicular to FIG. 2.

Before making an incision, a surgeon often marks the cornea with an ink tolerable to an eye and particularly to the corneal environment. Over the years, various designs have sought to mark a cornea. The prior art includes tubular guides placed upon the eye, guidance cards, knife arrays, and the like. The patent to Grandon, U.S. Pat. No. 4,739,761 describes a cornea marking device. This device has its paired blades 32a, 32b, as a unit with the supporting frame 30a as in FIG. 3. The blades have orientations on multiple meridians as shown in FIGS. 4-7. FIG. 3 also shows Grandon's blades within the diameter of the supporting frame so that the blade assembly 30 fits as a unit into the inner edge 44 of the base plate 41. However, FIG. 10 shows the Grandon blades as extending beyond the supporting frame. These wider blades join to the frame 30a as a unit for insertion through the opening 43 in FIG. 9. Grandon's device has blades on the 0, 45, 90, 135, 180, 225, 270, and 315 meridians. Grandon's patent lacks a top viewable dial with ridges for manual turning of the blades while Grandon's device has more of a "drop in" blade assembly with little manual turning foreseen.

The patent to Soloviev of Soviet Russia, U.S. Pat. No. 4,417,579, discloses a cornea marking device. This device has a cylindrical sight 4 with cross hairs 5 and a rotatable ring 1 with a flange 7 that holds marking blades 8 with a curvature, col. 3 line 1, see FIG. 1. The device also has an embodiment with gradations 12 visible on a drum 11. Presumably the drum 11 is fixed to the sight 4 while the ring has a window to view the gradations. The patent generally shows many blades with a few pairs of blades upon a diameter of the ring. The patent shows the gradations generally perpendicular to the blades. The patent does not show ridges upon the sight, drum, or flange. However, the gradations in this patent though require removal of the device from the patient for adjustment by the surgeon.

The patent to Cress, U.S. Pat. No. 5,184,405, shows a calculator for fitting toric contact lenses. This calculator has a card 18 shown in FIG. 6 with a marked projector dial 26 joined to a transparent dial 25 through a common hub 28. The calculator has a window 20 that displays a prescription for the contact lens. The card has a generally planar form and rectangular shape.

The patent to Sugita of Japan, U.S. Pat. No. 5,314,439, shows a host cornea marking device. This device has telescoping tubes with four marking blades 14, spaced radially, generally orthogonally, see FIGS. 1, 4. An operator places the device upon a cutting on a recipient patient's cornea, centers the device, and then presses the outer tube and its blades upon the recipient's eye to emplace the marks, see col. 5 lines 1-15. This device utilizes four blades as shown.

The patent to Farah of Lebanon, U.S. Pat. No. 6,217,596, provides a corneal surface marking tool. This tool has a handle extending to a semicircular head having markers, or blades, as at 7, 9, 11. The handle also has an inclinometer 15, see FIG. 2 and col. 3 lines 49-60. The inclinometer guides the operator to position the tool so the head attains its relationship to a vertical axis from the pupil of a corneal surface. This patent shows blades in fixed positions not subject to rotations.

Figure 4:
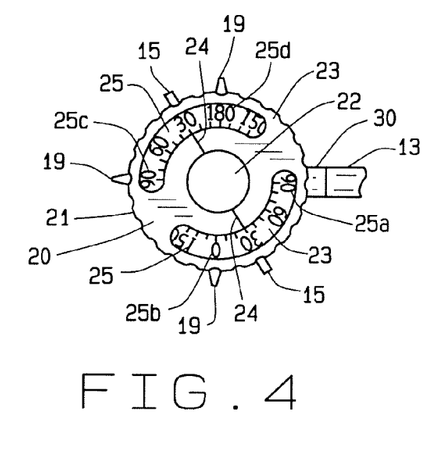
FIG. 4 illustrates a top view of the head of the invention.

The patent to Villasenor, U.S. Pat. No. 4,406,285, discloses an apparatus for guiding a blade during keratotomy. This apparatus includes a semi-spherical template with a plurality of radial slits upon it. The template has its thickness that cooperates with blade length and patient corneal thickness to avoid the blade penetrating Descemet's membrane as shown in FIG. 4. Though this patent shows radial slits, it does not have blades.

The patent to Warren, U.S. Pat. No. 4,440,168, shows us a surgical device for use on bone. This device has a handle 36 connected to a body 10. Within the body 10 a member 20 receives a blade 62 that marks body tissue, often by application of a mallet. The member 20 rotates to different angulations measured on indicia 40 and positioned by indents and ball bearings. This device has a single blade perpendicular to the handle on two axes. The device allows the blade to slide axially. This patent does not show dual blades at an angle to the handle.

And, the patent to Fedorov of Soviet Russia, No. 4,515,157, describes a corneal incision marker. This marker has a case 1 with threads 9 that engages a nut 7. Within the case, the marker has a plurality of holders 4 generally arrayed radially. Each holder has a marker 2 with an edge 3. The holders have a beveled geometry at 5 that deflects the holder and marker as the nut changes axial position along the threads 9. The marker has gradations as at 11 and shows threaded advancement of the nut upon the case. This marker adjusts the angle of its markers.

The present invention overcomes the disadvantages of the prior art and provides a toric axis marker that allows a surgeon to adjust the marker's position relative to its handle without inverting the marker or removing the marker from the corneal vicinity. The present invention allows a surgeon to adjust the marker to a setting then to place it upon the cornea of an eye and then readily adjust the marker.

SUMMARY OF THE INVENTION

Generally, the toric axis marker has a handle for gripping by a surgeon, a tip coaxial with the handle, a head upon the tip, a dial axially above the head, and a marker head with two blades beneath the head and connecting axially to the dial. The dial and blades rotate simultaneously and concentrically upon the head. The head and its components have a central aperture for a surgeon to use in guiding the marker into position relative to the center of an eye. The marker head has its two blades upon a common diameter. The surgeon using the marker sees its adjustment from above. The dial has two symmetric arcuate windows that reveal angle notations upon a marker body of the head beneath it. The marker body remains fixed relative to the handle and generally at an inwardly offset angle to the longitudinal axis of the handle. Upon turning the dial using its grip edge, the blades move with the marker head and the dial and attain their orientation relative to protrusions upon the marker body. Each blade has a blunt edge outwardly from the marker head and a slightly curved shape that conforms to the aspherical shape of a typical eyeball, proximate the cornea. Upon turning the dial the two blades rotate about a common centerline through the aperture usually towards a protrusion. With the blades positioned and usually coated with an ink, a surgeon marks the cornea with an ink to note the desired position of incisions for RK or placement of a new lens.

The present invention has at most a gentle affect upon the epithelium which minimizes infection risk. Additional features of the invention will be described hereinafter and which will form the subject matter of the claims attached.

Numerous objects, features and advantages of the present invention will be readily apparent to those of ordinary skill in the art upon a reading of the following detailed description of the presently preferred, but nonetheless illustrative, embodiment of the present invention when taken in conjunction with the accompanying drawings. Before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, the phraseology and terminology employed herein are for the purpose of description and should not be regarded as limiting.

One object of the present invention is to provide a toric axis marker that allows a surgeon to adjust its angular position without inverting the marker.

Another object is to provide such a toric axis marker that marks a cornea without incising it.

Another object is to provide such a toric axis marker that positions its marking head generally tangent to a cornea yet has its handle comfortably in the grasp of a surgeon.

Another object is to provide such a toric axis marker that has a reasonable cost of manufacturing so the purchasing ophthalmologists, clinics, hospitals, and organizations can readily buy the toric axis marker through catalogs, suppliers, vendors, and supply sources.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated a preferred embodiment of the invention.

BRIEF DESCRIPTION OF THE DRAWINGS

In referring to the drawings.

The same reference numerals refer to the same parts throughout the various figures.

DESCRIPTION OF THE PREFERRED EMBODIMENT

Figure 1:
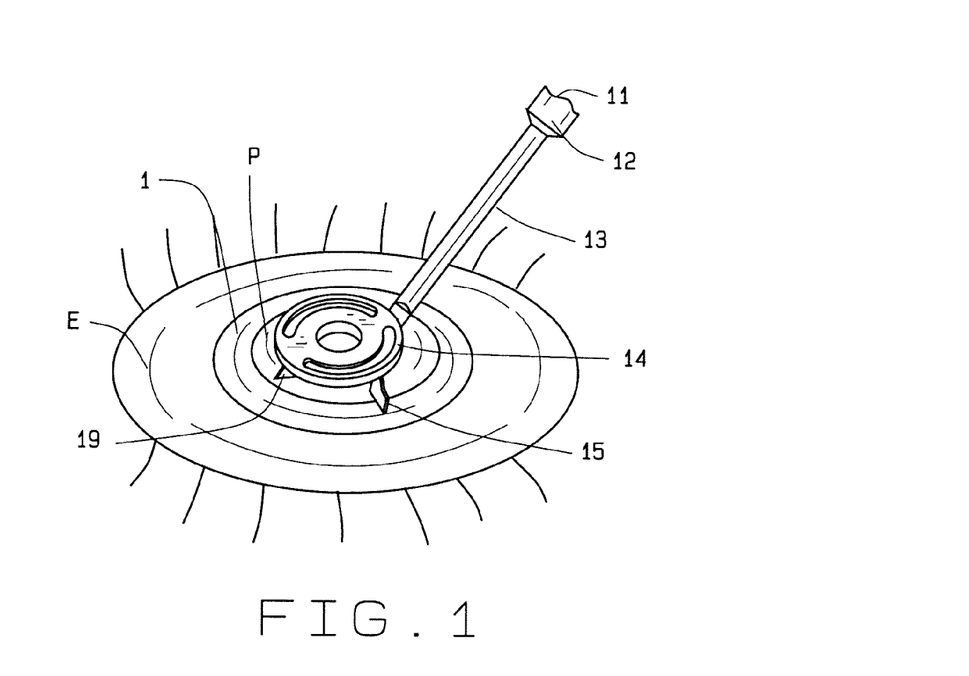
FIG. 1 shows a perspective view of the invention near an eye.

The present art overcomes the prior art limitations by providing a toric axis marker that marks a cornea without the user, or surgeon, inverting the marker. As this description and drawings relate to a tool used proximate a human eye with some dimensions being small, the drawings show an enlarged view of the invention. A person has an eye E as shown in FIG. 1 that may develop a condition calling for marking of the E. The eye E has the usual eyelashes upon each eye lid, here shown spaced apart, revealing an iris I and its pupil P centered therein. The user grasps a handle 11 of the invention and positions its head 14 above the eye E generally centered upon the pupil P. The handle has an approximately length of 127 millimeters. The handle has a shoulder 12 upon one end, as later described, and a tip 13 extending outwardly from the shoulder and coaxial with the handle. Opposite the shoulder, the tip joins to the head 14, generally upon a radius through the center of the head. Beneath the head, the marker has two collinear blades 15 generally perpendicular to the head. Grasping the handle with dexterity, the user then gently places the blades 15 of the head 14 upon the eye E and marks a meridian upon the cornea of the eye beneath the blades. The marking blades 15 have a shape and cross section, as later shown and described, that retains a dye, which permits a user to mark the patient's cornea with the lightest of touch. The blades extend outwardly approximately 1 millimeter from a dial 20 for ready and easy observation by the user.

Figure 2:
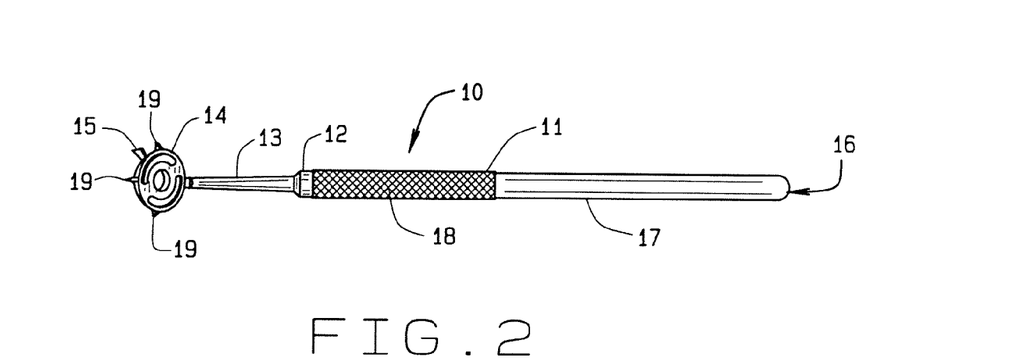
FIG. 2 describes a front view of the invention.

Turning to the toric axis marker, or invention 10, shown in FIG. 2, the invention 10 generally has a slender, elongated form with a working head 14 towards one end of the handle 11 and an opposite back 16. The back is generally located outwardly from a user's thumb upon properly grasping the instrument. The handle has an aft portion 17 beginning at the back 16 and proceeding towards the head. The aft portion has a generally smooth surface and extends to approximately half the length of the invention 10. The handle has a fore portion 18 extending from the aft portion to the shoulder 12. The fore portion has knurling to assist the grip of the user and extends for less than half the length of the invention. The aft portion and the fore portion are generally of round cross section and the fore portion has a slightly larger diameter. Opposite the back, the fore portion merges into the shoulder 12 of lesser diameter than the fore portion. The shoulder then tapers abruptly to the tip 13. The tip also tapers from its maximum diameter proximate the shoulder to its minimum diameter proximate the head 14. The tip, shoulder, fore portion, back portion, and back are all coaxial and collinear as shown. A longitudinal axis of the invention 10 extends for its length from the back, through the handle and into the tip. The length of the invention 10 also follows the longitudinal axis.

Opposite the shoulder upon the tip, the head 14 joins to the minimum diameter of the tip. The head has an angled joint to the tip so that the head rotates 45° towards the shoulder 12, that is, the plane of the head rotates 45° upwardly from the longitudinal axis of the invention 10. The head includes three protrusions 19, or alignment blades, or non-marking reference blades, that extend outwardly from the head. One protrusion has an orientation in a plane with the longitudinal axis of the invention 10 and is somewhat opposite the handle 11. The other pair of protrusions is generally 90° in orientation from the first protrusion described and 90° away in orientation from the longitudinal axis of the handle. Generally the protrusions, here show towards the left, the head has its two coplanar marking blades 15. The blades also have an orientation 90° away in orientation from the longitudinal axis of the handle and also have an orientation relative to the first protrusion described. A user may set the orientation of the blades by turning a portion of the head 14, later described, with the other hand of the user not grasping the handle 11 while the user maintains the invention 10 proximate an eye E during usage.

As previously mentioned, the head 14 joins to the minimum diameter of the tip and extends away from the tip and the majority of the handle 11 as shown in FIG. 3. The head extends from the tip at 45° angle towards the shoulder 12, that is, the plane of the head rotates 45° upwardly from the longitudinal axis of the invention 10. The orientation of the head relative to the handle allows a user to position the head over the pupil of an eye while having the user's hand away from the eye. This figure also shows the marking blades 15 being collinear pair and beneath the protrusions, that is, away from the head. The marking blades have a shape that approximates the curvature of the corner as later shown in FIGS. 5, 7, 8.

Viewing the head 14 more closely, FIG. 4 shows what a user sees when operating the invention 10. The tip has its minimal diameter approximate the head 14. The tip merges into a neck 30 of the head. The neck has a coaxial and collinear orientation to the longitudinal axis of the hand. The neck also commences the angled orientation of the head as previously described and shown in FIGS. 2, 3. Outwardly from the neck, the head has a dial 20 with a generally annular shape, generally round with an outer diameter and an inner diameter. The dial has a grip edge 21 upon its circumference that has a pattern of ridges or other relief that aids a user's grip with turning the dial. A user can pre-set the dial within seconds unlike in the prior art of turning an instrument over to view its markers while simultaneously attempting to grasp and align them with a gauge on the other side of the prior art instrument. The maximum extent of the grip edge defines the outer diameter of the dial, approximately 12.8 millimeters. The inner diameter of the dial defines an aperture 22 having a generally round shape that extends through the head 14 of the invention 10. The aperture allows a user visually to position and to align the head above a patient's pupil. The aperture is centered upon the head and a diameter through the aperture is coaxial with the longitudinal axis of the invention. The inner diameter is preferably 9.0 millimeters. Outwardly from the aperture, the dial has two arcuate windows 23. The windows extend for approximately 125 degrees of arc and have a symmetric arrangement about the aperture. The windows are also mutually spaced apart. Each window has an outer radius and an inner radius so that the outer radius is slightly less then the outer diameter of the dial and the inner radius exceeds the inner diameter of the dial. The windows exclude the material of the dial and allow a user to see through the dial. Dividing each window in half along its arcuate length, each window has a guide 24 extending radially from the window across the dial towards the aperture. Each guide has a length spanning from the inner radius of the window to the inner diameter to the aperture. The guides of each window have a collinear orientation.

Through each window, the head displays a portion of a scale 25. The scale illustrates the angular orientation of the dial relative to an imaginary line transverse the longitudinal axis of the marker 10. The scale measures 0° to 180° of angular rotation in 10° increments and allows setting of the marking blades to within at least 2° of a desired meridian. The scale begins with a 90° mark, as at 25a, collinear with the longitudinal axis of the marker 10 and centered upon the neck 30 and the tip 13. Clockwise from the 90° position, the scale declines at a regular arcuate interval to the 0° position, as at 25b, generally transverse to the longitudinal axis of the marker 10 and towards the left of the handle 11 when held in the right hand of a user. As shown in the drawing, and in reference to a dial clock, the 0° position would be at the 6 o'clock position. Continuing clockwise from the 0° position, the scale decreases at its regular arcuate interval to the second 90° position, as at 25c, collinear with the longitudinal axis of the marker 10, centered upon the neck 30 and the tip 13, but opposite the neck. As shown in the drawing, and in reference to a dial clock, the second 90° position would be at the 9 o'clock position. Continuing once more clockwise from the second 90° position, the scale decreases at its regular arcuate interval to the 180° position, as at 25d, opposite the 0° position, generally transverse to the longitudinal axis of the marker 10 and towards the right of the handle 11 when held in the right hand of a user. As shown in the drawing, and in reference to a dial clock, the 180° position would be at the 12 o'clock position. Continuing lastly clockwise from the 180° position, the scale decreases at its regular arcuate interval to the 90° position, as at 25a, where the scale began. As shown in the drawing, and in reference to a dial clock, the 90° position would be at the 3 o'clock position. The guides 24 of the dial provide a visual cue to the user of the orientation of the marking blades 15 beneath the protrusions 19 and opposite the dial. The scale has its progression of angular references so that the guides show the same numeric angle in both windows, except for the 0° and 180° positions. Using those two different positions aids the user in orienting the marker 10 to the user's left and right. Beneath the 0°, second 90°, and 180° positions, the head has the protrusions 19 that extend outwardly from the dial 20, particularly from the grip edge 21. The protrusions provide another aid, both visual and tactile, to the user for orienting the marker 10 during usage.

Figure 5:
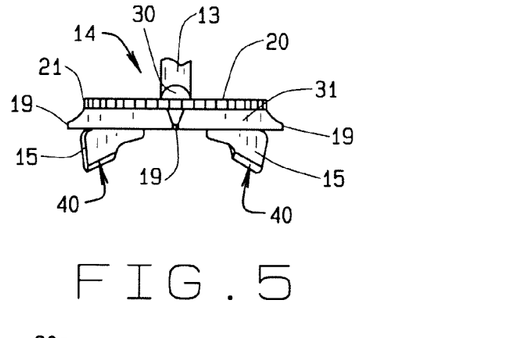
FIG. 5 shows a front view of the head of the invention.

FIG. 5 shows the head 14 in a front view, that is, head on, with the protrusion 19 at the second 90° position in the foreground and the protrusion 19 at the 0° position to the right of the figure. The tip 13 extends outwardly from the handle, not shown, to the neck 30 that merges to the center of the head at a marker body 31. The marker body has a somewhat rounded shape with an outer diameter less than that of the outer diameter of the dial. However, the marker body extends outwardly in its diameter forming the three protrusions 19 shown. The protrusions have a generally tapered cross section as in the two protrusions to the left and the right in this figure. Each protrusion has its maximum extent beneath the dial 20, that is, just above the blades. The protrusion shape provides another visual and tactile aid to the user. Above the marker body 31, the head has the dial 20 with its grip edge 21 here shown on edge. The dial, particularly beneath the guides 24, holds the two spaced apart marking blades 15. Each blade 15 has a rounded marking edge 40 that retains an ink and when placed upon a patient's cornea, delivers the ink to the cornea as a precise line and without incising the cornea. The marking edges generally have a shape and orientation that follows the curvature of the cornea however, the marking edges are generally a mirror image of each other.

Figure 6:
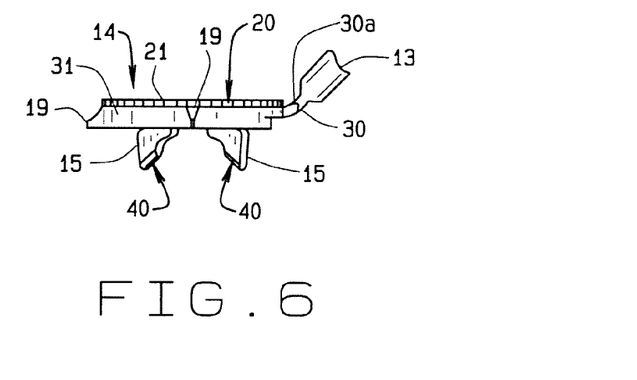
FIG. 6 describes a side view of the head of the invention.

Turning the marker 10 perpendicular to that shown in FIG. 5, FIG. 6 shows the head 14 in a side view with the handle to the right, that is, with the protrusion 19 at the 0° position, or as at 25b, in the foreground and the protrusion 19 at the second 90° position, or as at 25c to the left of the figure, opposite the handle. The marker body 31 has its form as described above with the blades 15 beneath the marker body and the dial 20 about the marker body. A user grasps the dial 20 at the grip edge 21 upon the dial's perimeter and the blades 15 move with the dial as it turns. Each blade has its marking edge 40 in a generally arcuate orientation that approximates the curvature of a cornea. The marker body 31 joins to the rest of the marker 10 through the neck 30 at the tip 13. The neck extends outwardly from the marker body beneath the first 90° position, as at 25a, and generally parallel to surface of the dial. The neck is generally opposite the second 90° position, as at 25c. Slightly away from the marker body, as at 30a, the neck angles upwardly, that is, towards the dial, at approximately 45°. Outwardly from the angle, the neck joins to the tip 13 of the handle 11 which a user grasps to operate the marker.

Figure 7:
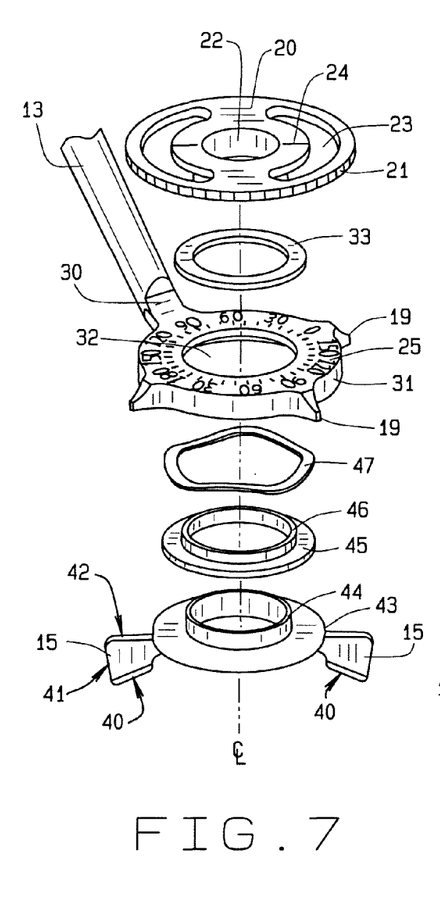
FIG. 7 shows an angled exploded view of the head of the invention.
Figure 8:
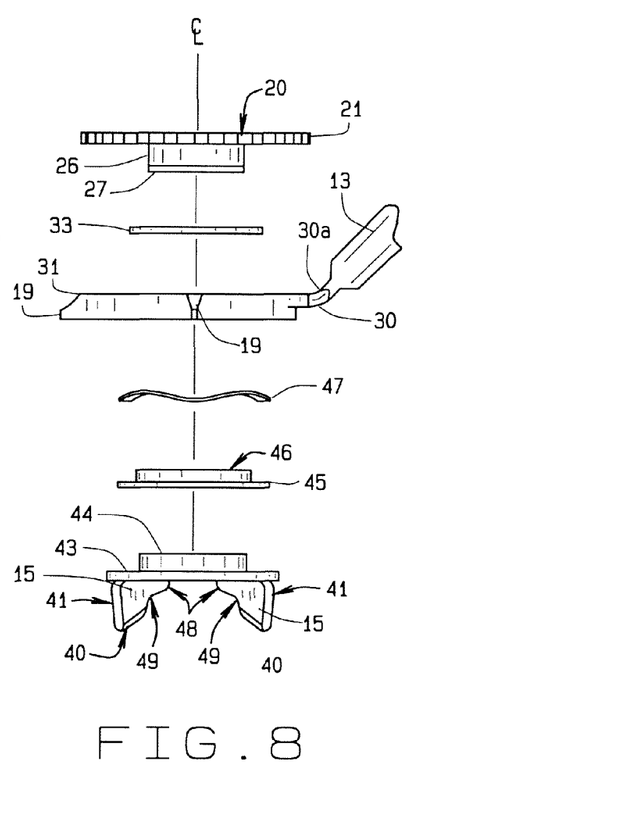
FIG. 8 shows an exploded side view of the head of the invention.

Having described the marker of the invention 10 as assembled, FIGS. 7, 8 show the marker 10 in exploded views that illustrate additional components of the invention. FIG. 7 shows an angled exploded view with the handle towards the left and the angle of the view generally along the 55° position of the marker body 31. The marker begins with its blades 15, generally two in number and spaced apart on a common diameter and being coplanar. Each blade has its marking edge 40 here shown as mirror images to approximate a cornea's curvature. The marking edges are generally rounded over to avoid incising the cornea while retaining ink during positioning of the marker prior to marking and releasing the ink upon pressing the marking edges 40 upon the cornea. The rounded cross section of the marking edges prevents abrasion of the cornea during usage. The marking edges have a downward orientation away from the centerline of the marked. Away from the centerline, edge marking edge joins to an outer edge 41 nearly perpendicular to the marking edge. The outer edge extends upwardly from the marking edge and merges with an upper edge 42 through a rounded corner. The upper edge is generally parallel to the marker body 31. Each upper edge extends inwardly and joins to a marker head 43. The marker head has an annular shape with an inner radius and an outer radius, the outer radius being less than half the diameter of the marker body. The marker head has its thickness, that is, dimension perpendicular to either radius, similar to the thickness of a blade 15. Extending upwardly from the marker head and opposite the blades, a collar 44 has its height above the marker head generally at least twice the thickness of the marker head. The collar has a generally hollow cylindrical form. Upwardly from the marker head 43, a second washer 45 fits upon the collar 44. The second washer has a generally flat annular form with an outer radius less than that of the marker head and a second collar 46 extending upwardly from the second washer defining the inner radius of the second washer. The second collar fits snugly upon the collar 44 of the marker head. Upwardly from the second washer, the marker 10 has a spring washer 47. The spring washer has a generally undulating form with four crests shown and a narrow width where the outer diameter and the inner diameter are close. The inner diameter allows the spring washer to fit snugly upon the second collar 46. During assembly, the marker head, second washer, and spring washer fit concentrically upon the collar 44 so that the marking blades 15 extend outwardly from beneath the marker body 31.

The marker body shown in FIG. 7 includes a second aperture 32 generally centered in the marker body and with its diameter. The diameter of the second aperture admits the second collar 46 when assembled. As before, the marker body has a generally rounded form but with three protrusions 19 spaced equiangularly and defining the 0° position, second 90° position, 180° position, and first 90° position at the neck 30 of the tip 13. The neck extends upwardly from the plane of the marker body to offset the tip and the handle for the comfort of the user. The four cardinal positions and intermediate angular positions appear on the scale 25 upon the top of the marker body, that is, opposite the marker head 43 and the blades 15. Each blade 15 extends about 1 millimeter outwardly from the head 43 for ready visibility by the user for placement upon a preselected meridian. As previously described and shown, the scale appears visible through two windows in the dial for a user to select the orientation of the blades relative to the longitudinal axis of the handle. Upwardly from the marker body, the marker 10 has a washer 33, generally flat and annular of a thin width. The washer has an outer diameter slightly more than the diameter of the second aperture 32. The washer has an inner diameter that admits a feature of the dial as later shown. Upwardly from the washer, the marker has its dial 20 of a generally round shape with the grip edge 21 upon its perimeter for grasping by a user. Inwardly from the grip edge slightly, the dial has its two windows 23 generally arranged symmetrically. The dial has dual axis symmetry when viewed from above. Each window has a guide 24 generally extending upon a common diameter from the inner edge of the window to the aperture 22. The aperture has its inner diameter through which a user gazes to operate the invention while looking at a patient's pupil through the inner diameters of the washer, spring washer, second washer, and marker head.

And turning to FIG. 8 which shows an exploded side view of the marker, the tip 13 appears to the right in this figure with the protrusion at the second 90° position in the foreground and along the centerline of the of the marker 10. As above, the marker 10 has its dial 20 with a generally round shape and its grip edge 21 upon the perimeter. Below the top of the dial, that is, the surface with the guides, the dial has a centered hollow bushing 26. The bushing has a cylindrical form and a height greater than the thickness of the dial, that is, the height of the grip edge. Preferably, the bushing has a height proximate that of the marker body. Opposite the dial's surface, the bushing has a leading edge 27 upon its circumference. The leading edge may include a bevel, chamfer, or rounding over so that the bushing fits through the washer 33 and then into the second aperture 32 of the marker body 31. The marker body has the three protrusions 19 as described and the neck 30 to the right in this figure that angles upwardly 45°, as at 30a, to the tip 13. Through the marker body, the bushing passes into the spring washer 47 and into the second collar 46 of the second washer 45. The leading edge of the bushing then engages the collar 44 of the marker head 43. The dial, its bushing, the washer, marker body, spring washer, second washer, and marker head, are assembled concentrically and in a press fit to medical instrument grade tolerances so that the blades follow the angle set by the dial upon the scale.

FIG. 8 also shows the blades in more detail. Each blade has a somewhat thickened L shape when viewed from the front as previously shown in FIG. 7. Each blade begins with the long portion of the L shape, that is, the upper edge 42, joining perpendicular to the marker head 43. Each blade extends outwardly to the outer edge 41 and then downwardly to the marking edge 40. The outer edge and marking edge form the short portion of the L shape. The marking edge extends inwardly but for less than the length of the upper edge. The blade then narrows to the lower edge 49 that transitions from the marking edge 40 to an inner edge 48 generally opposite the outer edge but of less length than the outer edge. The inner edges of the two blades have a spacing that allows an unobstructed view through the marker by a user when positioning the blades to mark the cornea of a patient prior to an incision during a keratotomy procedure for vision improvement.

From the aforementioned description, a toric axis marker has been described. The toric axis marker is uniquely capable of marking a cornea with ink at an angle selected by the user directly without inverting the instrument. The toric axis marker and its various components may be manufactured from many materials, including but not limited to, polymers, polyethylene, polypropylene, ferrous and non-ferrous metals, their alloys, and composites. The components may be of surgical grade and with anti-microbial characteristics.

As such, those skilled in the art will appreciate that the conception, upon which this disclosure is based, may readily be utilized as a basis for the designing of other structures, methods and systems for carrying out the several purposes of the present invention. Therefore, the claims include such equivalent constructions insofar as they do not depart from the spirit and the scope of the present invention.

The preceding assembly steps and dimensional parameters remain as estimates by the Applicant calculated with accepted engineering and optics formulas using reasonable assumptions and appropriate simplifications. The Applicant asserts that the assembly steps and dimensional parameters have not approached finality but rather show that the assembly steps and dimensions of the invention may have a plausible adjustment given known engineering and optics principles. Actual assembly steps and dimensional parameters will remain within a range of the values provided here.

Various aspects of the illustrative embodiments have been described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations have been set forth in order to provide a thorough understanding of the illustrative embodiments. However, it will be apparent to one skilled in the art that the present invention may be practiced without the specific details. In other instances, well known features are omitted or simplified in order not to obscure the illustrative embodiments.

Various operations have been described as multiple discrete operations, in a manner that is most helpful in understanding the present invention, however, the order of description should not be construed as to imply that these operations are necessarily order dependent. In particular, these operations need not be performed in the order of presentation.

Moreover, in the specification and the following claims, the terms "first," "second," "third" and the like are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to ascertain the nature of the technical disclosure. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

I claim:

1. A corneal marking device, comprising:
    an elongated slender handle, said handle having a back and an opposite shoulder, a tip extending outwardly from said shoulder opposite said back, said tip being coaxial with said shoulder and said back;
    a head, extending from said tip generally opposite said shoulder wherein said head marks a cornea with ink;
    said head having a centered aperture wherein said aperture allows a user to see through said device, two spaced apart coplanar marking blades, said marking blades being dull and configured to receive ink, and a dial including said aperture and connecting to said blades wherein said dial is visible to a user;
    said dial having a generally round shape with an outer diameter and an inner diameter, the inner diameter of said dial defining said centered aperture, a grip edge upon the circumference of said dial, at least one arcuate window allowing visibility through said dial, said at least one arcuate window having its outer diameter slightly less than the outer diameter of said dial and its inner diameter more than the inner diameter of said dial, said at least one arcuate window extending for at least ninety degrees of arc;
    a marker head including said marking blades and connecting beneath said dial, said marker head having a generally round annular flat shape, said marking blades extending outwardly from said marker head, a collar of a hollow cylindrical shape centered upon said marker head and extending outwardly from said marker head, said blades joining to said marker head opposite said collar generally perpendicular to the annular flat shape; and, a marker body, generally round in shape, having a thickness and at least one protrusion extending radially from said marker body, and at least one scale, wherein said at least one scale is visible through said at least one window.

2. The corneal marking device of claim 1 further comprising:
said head having said dial, a washer beneath said dial, said washer abutting said marker body, a spring washer beneath said marker body, a second washer beneath said spring washer, and said marker head beneath said second washer;
wherein said dial, said washer, said spring washer, said second washer and said marker head assemble concentrically upon said marker body.

3. The corneal marking device of claim 1 further comprising:
said dial having two arcuate windows and a bushing generally of hollow cylindrical shape extending away from said dial.

4. The corneal marking device of claim 3 wherein said arcuate windows are bi-axially symmetrically arranged upon said dial and said dial has two collinear spaced apart guides each of said guides extending from the inner diameter of each window to the inner diameter of said dial wherein said guides are generally aligned with said blades beneath said marker body.

5. The corneal marking device of claim 1 wherein
each of said blades having a generally L like shape including a marking edge connecting to an outer edge connecting to an upper edge connecting to an inner edge connecting to a leading edge, said leading edge returning to said marking edge;
said outer edge being generally perpendicular to said upper edge and spaced outwardly from said inner edge, said outer edge having a greater length than said inner edge;
said upper edge being spaced apart from said marking edge, said upper edge having a greater length than said marking edge;
said marking edge having a cross sectional shape preventing incision of a cornea and allowing deposit of ink upon a cornea;
said marking edge being at an acute angle to said upper edge; and,
said blades being mutually spaced apart and positioned in mirror image beneath said marking head.

6. The corneal marking device of claim 1 wherein said marker body is at an angle to said handle.

7. The corneal marking device of claim 6 wherein said marker body is at a 45° to said handle.

8. A corneal marking device, comprising:
a head capable of marking a cornea of a patient with ink upon a preselected meridian, said head having a centered aperture wherein said aperture allows a user to see through said device, two spaced apart coplanar marking blades, said marking blades being dull and configured to receive ink, and a dial including said aperture and connecting to said blades wherein said dial is visible to a user;
said dial having a generally round shape with an outer diameter and an inner diameter, the inner diameter of said dial defining said centered aperture, a grip edge upon the circumference of said dial, at least one arcuate window allowing visibility through said dial, said at least one arcuate window having its outer diameter slightly less than the outer diameter of said dial and its inner diameter more than the inner diameter of said dial, said at least one arcuate window extending for at least ninety degrees of arc;
a marker head including said marking blades and connecting beneath said dial, said marker head having a generally round annular flat shape, said marking blades extending outwardly from said marker head, a collar of a hollow cylindrical shape centered upon said marker head and extending outwardly from said marker head, said marking blades joining to said marker head opposite said collar generally perpendicular to the annular flat shape; and,
a marker body, generally round in shape, having a thickness and at least one protrusion extending radially from said marker body, and at least one scale, wherein said at least one scale is visible through said at least one window.

9. The corneal marking device of claim 8 further comprising:
said head having said dial, a washer beneath said dial, said washer abutting said marker body, a spring washer beneath said marker body, a second washer beneath said spring washer, and said marker head beneath said second washer;
wherein said dial, said washer, said spring washer, said second washer and said marker head assemble concentrically upon said marker body.

10. The corneal marking device of claim 8 further comprising:
each of said blades having a generally L like shape including a marking edge connecting to an outer edge connecting to an upper edge connecting to an inner edge connecting to a leading edge, said leading edge returning to said marking edge;
said outer edge being generally perpendicular to said upper edge and spaced outwardly from said inner edge, said outer edge having a greater length than said inner edge;
said upper edge being spaced apart from said marking edge, said upper edge having a greater length than said marking edge;
said marking edge having a cross sectional shape preventing incision of a cornea and allowing deposit of ink upon a cornea;
said marking edge being at an acute angle to said upper edge; and,
said blades being mutually spaced apart and positioned in mirror image beneath said marking head.

11. The corneal marking device of claim 8 further comprising:
an elongated slender handle, said handle having a back and an opposite shoulder, a tip extending outwardly from said shoulder opposite said back, said tip being coaxial with said shoulder and said back, said tip joining to said head at an angle to a length of said handle.

12. The corneal marking device of claim 8 further comprising:
said dial having two arcuate windows and a bushing generally of hollow cylindrical shape extending away from said dial, said arcuate windows having bi-axial symmetry upon said dial, said dial having two collinear spaced apart guides, each of said guides extending from the inner diameter of each arcuate window to the inner diameter of said dial;
wherein said guides are generally aligned with said blades beneath said marker body; and, wherein said marking blades extend outwardly from said marker head.

13. A device for marking the cornea of a patient's eye, said device comprising:

an elongated slender handle, said handle having a back and an opposite shoulder, a tip extending outwardly from said shoulder opposite said back, said tip being coaxial with said shoulder and said back;

a head, extending from said tip generally opposite said shoulder wherein said head marks a cornea with ink and extending at a 45° to said handle;

said head having a centered aperture wherein said aperture allows a user to see through said device, two spaced apart coplanar marking blades, said marking blades being dull and configured to receive ink, said marking blades being mutually spaced apart and positioned in mirror image beneath said marking head;

said head having a dial including said aperture and connecting to said blades wherein said dial is visible to a user, said dial having a generally round shape with an outer diameter and an inner diameter, the inner diameter of said dial defining said centered aperture, a grip edge upon the circumference of said dial, two symmetrically spaced arcuate windows allowing visibility through said dial, said arcuate windows each having an outer diameter slightly less than the outer diameter of said dial and an inner diameter more than the inner diameter of said dial, each of said windows extending for at least ninety degrees of arc, said dial having two collinear spaced apart guides, each of said guides extending from the inner diameter of one of said arcuate windows to the inner diameter of said dial, wherein said guides are generally aligned with said blades beneath said marker body, said dial having a bushing generally of hollow cylindrical shape extending away from said dial;

a marker head including said marking blades and connecting beneath said dial, said marker head having a generally round annular flat shape, said marking blades extending outwardly from said marker head, a collar of a hollow cylindrical shape centered upon said marker head and extending outwardly from said marker head, said blades joining to said marker head opposite said collar generally perpendicular to the annular flat shape;

a marker body, generally round in shape, having a thickness and at least one protrusion extending radially from said marker body, and at least one scale, wherein said at least one scale is visible through said arcuate windows;

said marker head having said dial, a washer beneath said dial, said washer abutting said marker body, a spring washer beneath said marker body, a second washer beneath said spring washer, and said marker head beneath said second washer, wherein said dial, said washer, said spring washer, said second washer and said marker head assemble concentrically upon said marker body;

each of said blades having a generally L like shape including a marking edge connecting to an outer edge connecting to an upper edge connecting to an inner edge connecting to a leading edge, said leading edge returning to said marking edge, said outer edge being generally perpendicular to said upper edge and spaced outwardly from said inner edge, said outer edge having a greater length than said inner edge, said upper edge being spaced apart from said marking edge, said upper edge having a greater length than said marking edge, said marking edge having a cross sectional shape preventing incision of a cornea and allowing deposit of ink upon a cornea, said marking edge being at an acute angle to said upper edge.

* * * * *